United States Patent
Rothman et al.

(10) Patent No.: US 8,288,524 B2
(45) Date of Patent: Oct. 16, 2012

(54) MOLECULAR DIAGNOSIS OF BACTEREMIA

(75) Inventors: Richard E. Rothman, Cockekysville, MD (US); Maulik D. Majmudar, Germantown, MD (US); Charlotte A. Gaydos, Bel Air, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/849,474

(22) Filed: Aug. 3, 2010

(65) Prior Publication Data

US 2011/0008791 A1 Jan. 13, 2011

Related U.S. Application Data

(63) Continuation of application No. 12/348,558, filed on Jan. 5, 2009, now abandoned, which is a continuation of application No. 09/940,860, filed on Aug. 29, 2001, now abandoned.

(60) Provisional application No. 60/229,376, filed on Aug. 31, 2000.

(51) Int. Cl.
*C07H 21/04* (2006.01)
*C12Q 1/68* (2006.01)
*C12P 19/34* (2006.01)

(52) U.S. Cl. .................... 536/24.33; 435/6.12; 435/91.2

(58) Field of Classification Search ........................ None
See application file for complete search history.

(56) References Cited

U.S. PATENT DOCUMENTS

| | | | |
|---|---|---|---|
| 5,407,797 A | | 4/1995 | Marliere et al. |
| 5,516,292 A | | 5/1996 | Steinman |
| 5,571,674 A | | 11/1996 | Hoshina et al. |
| 5,654,141 A | | 8/1997 | Mariani et al. |
| 5,994,066 A | | 11/1999 | Bergeron et al. |
| 6,001,564 A | | 12/1999 | Bergeron et al. |
| 6,054,278 A | * | 4/2000 | Dodge et al. .................... 435/6 |
| 6,184,000 B1 | | 2/2001 | Jones et al. |
| 6,261,769 B1 | * | 7/2001 | Everett et al. .................... 435/6 |
| 6,395,475 B1 | * | 5/2002 | Leggett et al. .................... 435/6 |
| 7,255,989 B1 | * | 8/2007 | Jeannin et al. ................. 435/6.1 |

OTHER PUBLICATIONS

Lowe et al., A computer program for selection of oligonucleotide primers for polymerase chain reactions. Nucleic Acids Research, vol. 18, No. 7, pp. 1757-1761, 1990.*
Carroll, N.M. et al., "Elimination of Bacterial DNA from Taq DNA Polymerases by Restriction Endonuclease Digestion", Journal of Clinical Microbiology, vol. 37, No. 10, (1999), pp. 3402-3404.
Corless, C.E. et al., "Contamination and Sensitivity Issues with a Real-Time Universal 16S rRNA PCR", Journal of Clinical Microbiology, vol. 38, No. 5, (2000), pp. 1747-1752.
Lu, Jang-Jih, et al., "Use of PCR with Universal Primers and Restriction Endonuclease Digestions for Detection and Identification of Common Bacterial Pathogens in Cerebrospinal Fluid", Journal of Clinical Microbiology, vol. 38, (2000), pp. 2076-2080.
Sharma, J.K. et al., "A Simple Method for Elimination of Unspecific Amplifications in Polymerase Chain Reaction", Nucleic Acids Research, vol. 20, No. 22, (1992), pp. 6117-6118.
M. G. Bergeron et al., "Rapid Detection of Group B Streptococci in Pregnant Women at Delivery," The New England Journal of Medicine, Jul. 20, 2000, vol. 343, No. 3, pp. 175-179.
K. Sen et al., "Multiplex PCR for Detection of Enterobacteriaceae in Blood, Blood Components," Transfusion, Nov. 2001, pp. 1356-1364.
DeFilippes F. M., "Decontaminating the PCR," Biotechniques, 1991, vol. 10, No. 1, pp. 26, 28, and 30.
Dougherty et al., Restriction Endonuclease Digestion Eliminates Product Contamination in Reverse Transcribed Polymerase Chain Reaction, J. Virol. Methods, 1993, Vol. 41, pp. 235-238.
Dunbar et al., "Levels of Bacterial Community Diversity in Four Arid Soils Compared by Cultivation and 16S rRNA Gene Closing," App. Environ. Microbiol., 1999, vol. 65, No. 4, pp. 1662-1669.
Stratagene Catalog, 1995, pp. 301-303.

* cited by examiner

*Primary Examiner* — Prabha Chunduru
(74) *Attorney, Agent, or Firm* — Banner & Witcoff, Ltd.

(57) ABSTRACT

A highly specific assay can be used for the detection of bacteremia in the clinical setting. The ubiquitous background endogenous DNA present in all PCR reagents is eliminated using a restriction endonuclease digestion. Universal primers for eubacteria are used for detection, and specific primers or probes for bacterial species can be used for identification of species.

1 Claim, 5 Drawing Sheets

Figure 1A

| Primer Name | Sequence | Product size |
|---|---|---|
| PEU7 | 5' GCA AAC AGG ATT AGA TAC CC 3' (787-806) | 416bp |
| PEU8 | 5' GGA GGA AGG CGA GGA TGA CG 3'(1381-1403) | |

Figure 1B

```
              [          PEU7 --->        ]
        786   agcaa  acagg  attag  atacc  ctggt  agtcc   815

S. aureus     .t...  .....  .....  .....  .....  .....
S. pneumoniae .....  .....  .....  .....  .....  .....
C. pneumoniae .....  .....  .....  .....  .....  .....
K. pneumoniae .....  .....  .....  .....  .....  .....
C. trachomatis.....  .....  .....  .....  .....  .....
E. coli       .....  .....  .....  .....  .....  .....
M. pneumoniae .....  .t...  .....  .....  ..a..  .....
Bacillus      ...g.  .....  .....  .....  .....  .....

[          <---PEU8          ]
        1181  cagga  ggaag  gcgag  gatga  cgtca  agtca
                                                  1205

S. aureus     .c...  .....  .t.g.  .....  .....  .a...
S. pneumoniae .c...  .....  .t.g.  .....  .....  .a...
C. pneumoniae .....  .....  .....  .....  .....  .....
K. pneumoniae .t...  .....  .t.g.  .....  .....  .....
C. trachomatis.....  .....  .....  .....  .....  .....
E. coli       .t...  .....  .t.g.  .....  .....  .....
M. pneumoniae tt...  .....  .aag.  .....  .....  .a...
Bacillus      .c...  .....  .t.g.  .....  .....  .a...
```

MOLECULAR DIAGNOSIS OF BACTEREMIA

This application claims priority to provisional U.S. Application Ser. No. 60/229,376, filed Aug. 31, 2000, the disclosure of which is expressly incorporated herein.

FIELD OF THE INVENTION

The invention relates to the field of clinical diagnostics. In particular, it relates to the field of detection of bacteremia in patients.

BACKGROUND OF THE INVENTION

There are an estimated 500,000 patients in the United States who develop bacteremia, with mortality rates ranging from 25-50%.[1] Early recognition and aggressive therapeutic intervention is known to significantly improve outcomes for those with systemic bacterial infections.[1] Unfortunately, no definitive clinical parameters or diagnostic assays currently exist that allow clinicians to rapidly and accurately identify patients with bacterial infections among those in whom systemic infections are suspected.

Patients with fulminant bacteremia are usually easily recognized by the presence of fever and significant vital sign abnormalities, described as sepsis syndrome. Early synthetic bacterial infections, or those which occur in vulnerable or immunosuppressed hosts may be more subtle however, leading to potential delays in diagnosis and treatment with associated increased risk for morbidity and mortality. Further, inherent limitations of the 'gold standard' diagnostic test for bacteremia, blood culture, renders it ineffective for guiding acute management decisions. These limitations include significant time delays associated with reporting of positive findings (typically at least 24-48 hours), relatively low sensitivity ranging from 30-50% among patients who meet criteria for sepsis syndrome, and diminished sensitivity in patients already on antibiotics.

The failure of either clinical judgment or diagnostic technology to provide quick and accurate data for identifying patients with bacteremia, leads most clinicians to follow a conservative management approach for those in whom systemic infection is suspected. Empiric intravenous antibiotic therapy offers the advantage of maximizing patient safety and improving outcomes for those later found to be bacteremic. Well known clinical examples in which patients are routinely hospitalized and given antibiotics while awaiting blood culture results include febrile episodes in infants, due to the high mortality associated with unrecognized septicemia, and any febrile illness in intravenous drug users due to the high risk of life-threatening infective endocarditis which is principally characterized by the presence of bacteremia. The benefits of conservative management may be offset however, by added costs and potential iatrogenic complications associated with treatment and hospital days for those later found not to be bacteremic, as well as increased rates of antimicrobial resistance. A rapid accurate assay for blood-borne bacterial infections which could be used to screen patients considered at risk would thus be invaluable for clinicians.

PCR, or polymerase chain reaction, is a technique which allows for rapid nucleic acid amplification and detection of small amounts of a target pathogen (e.g. bacterial RNA or DNA). Development of PCR diagnostics for clinical use have shown promise when primers for a specific pathogen are used in selected clinical settings. Examples include detection of *Mycobacterium tuberculosis* in patients with suspicious pulmonary infections, and identification of *Streptococcus pneumoniae* in children and infants with suspected septicemia from this organism. Numerous investigations have also been carried out employing a universal probe for more broad based bacterial identification. Findings published to date have principally been restricted to detection of bacteria in highly infected tissue specimens, e.g. resected heart valves in patients with suspected infective endocarditis, or clinical samples from an infected site such as an abscess. Unfortunately, less success has occurred with universal screening of blood samples, principally due to technical problems of the assay, most commonly related to contaminant bacterial DNA.

There is a need in the art for a rapid and sensitive test for detecting specific pathogens in clinical samples.

BRIEF SUMMARY OF THE INVENTION

According to one embodiment of the invention a pair of polymerase chain reaction primers for amplifying a 16S rRNA gene of eubacteria is provided. The primer pairs are selected from the group consisting of: PEU 7 and PEU 8 (SEQ ID NO 1 and 2), and PEU 4 and PEU 5 (SEQ ID NO: 3 and 4).

Another embodiment of the invention provides a method of performing polymerase chain reaction. Reagents for polymerase chain reaction are digested with a restriction endonuclease. The reagents comprise Taq DNA polymerase, deoxynucleotide triphosphates, reaction buffer, and primers. The primers have no recognition sites for the restriction endonuclease. The restriction endonuclease is inactivated under conditions that do not inactivate the Taq DNA polymerase. A test sample and the reagents for polymerase chain reaction are mixed to form a mixture. The mixture is subjected to conditions such that any templates present in the test sample which hybridize to both primers are amplified. Amplification product is detected. A detected amplification product indicates the presence of template which hybridizes to both primers in the test sample.

According to yet another embodiment of the invention a method of performing polymerase chain reaction is provided. Reagents for polymerase chain reaction are digested with AluI restriction endonuclease. The reagents comprise Taq DNA polymerase, deoxynucleotide triphosphates, reaction buffer, and a pair of primers selected from the group consisting of PEU7 and PEU 8 (SEQ ID NO: 1 and 2), and PEU 4 and 5 (SEQ ID NO: 3 and 4). The AluI restriction endonuclease is inactivated by heating the reagents to a temperature which inactivates AluI but does not inactivate Taq DNA polymerase. A test sample of DNA isolated from a patient's blood sample is mixed with the reagents for polymerase chain reaction to form a mixture. The mixture is subjected to conditions such that any templates present in the test sample which hybridize to both primers are amplified. Amplification product of 416 or 811 basepairs is detected. A detected amplification product indicates the presence of template which hybridizes to both primers in the patient's blood. This in turn indicates bacteremia in the patient.

The present invention also provides a kit for detecting bacteremia in a patient sample. The kit contains (1) a pair of primers which hybridize to opposite strands of 16S RNA of at least 10 eubacterial species, and (2) a restriction endonuclease which has a four base pair recognition site. The recognition site does not occur in either of the primers.

Another embodiment of the invention is a pair of primers which hybridize to opposite strands of 16S RNA genes of at least 10 eubacterial species at conserved regions. The primers prime synthesis of an amplification product comprising a non-conserved region of the 16S RNA which is distinctive for each of the at least 10 eubacterial species.

These and other embodiments of the invention provide the art with methods and tools for sensitively and accurately detecting bacterial microbes in a variety of sample types.

BRIEF DESCRIPTION OF THE DRAWINGS

FIGS. 1A and 1B provide a description and homology of PCR primers. FIG. 1A. Oligonucleotides (PEU7 (SEQ ID NO: 1) and PEU8 (SEQ ID NO: 2)) designed to target the highly conserved 16S rRNA region for universal amplification of bacterial DNA.

DETAILED DESCRIPTION OF THE INVENTION

It is a discovery of the present invention that ubiquitous contamination of reagents for nucleic acid amplification can be eliminated or reduced by treatment of the reagents with a restriction endonuclease which does not cleave or recognize a site within the implication primers, but desirably does cleave and recognize a site within the desired amplicon. Such a technique improves the sensitivity and specificity of PCR for detecting bacteremia in clinical samples, for example. The methods and tools disclosed can be used in other contexts, for example in the detection of environmental pathogens and food borne pathogens. Samples which are expected to harbor bacteria at low concentrations can be advantageously analyzed using the methods disclosed herein.

One of the major obstacles in transferring PCR technology from the laboratory to the clinical setting is the presence of ubiquitous 'contaminant' DNA, leading to frequent false-positive results. We have addressed this problem by incorporating a 'decontamination' step in our assay which decontaminates all reagents. Optionally one can use hot start Taq polymerase amplification, which also reduces contaminating amplification products. Any of a variety of techniques can be used to achieve a hot start amplification. In all methods Taq polymerase is prevented from synthesizing DNA until a suitable temperature is achieved that insures sufficient stringency of hybridization of primers to template. In one method enzyme is modified so that the increase in temperature during the first denaturation step of PCR causes a conformation change which activates the modified Taq. A second type of hot start technology employs antibody inhibition. An antibody cocktail specific for the polymerase active site can be added, and the steric hindrance of the antibody prevents polymerase activity. The antibody irreversibly denatures during the initial denaturation step. Still another method employs a physical barrier of wax to separate the primers from the polymerase; the wax is melted during the initial denaturation step.

There are four notable features which may be used to achieve a 'universal' PCR assay as disclosed herein. (1) Selection of a primer pair from the highly conserved 16S rRNA sequence, allowing for broad range bacterial amplification. (2) The presence of at least one recognition and/or cleavage site for a restriction endonuclease is desirable in the amplicon but not in the PCR primer set. This allows digestion or decontamination of all components of the PCR cocktail prior to PCR amplification. (3) Multiple copies of this restriction site within the amplified product is desirable because it increases the probability of cleaving contaminating DNA into 'nonamplifiable' product, thus diminishing the likelihood of amplifying background DNA which might contain a single point mutation in the restriction site. (4) Hot Start Taq DNA polymerase reaction is only activated at high temperatures (about 95° C.), preventing DNA polymerization from occurring during the decontamination step, which is performed at about 65° C.

A pair of primers can be used which hybridizes to opposite strands of 16S RNA genes of at least 10 eubacterial species at conserved regions. Such primers can hybridize to 5, 8, 12, 15, 20, 25, or 30 such species. Preferred species for hybridization are those which are prevalent in the context being analyzed. If clinical specimens are analyzed, then desirably the primers hybridize to the most important pathogens. Desirably the primers prime synthesis of an amplification product comprising a non-conserved region of said 16S RNA which is distinctive for each of the eubacterial species. The non-conserved regions provide the ability to determine which species is actually present and serving as the template for the amplification product. Preferably the amplification products contain at least one, two, three, or four recognition sites for a restriction endonuclease which is not present in said primers. The primers can be naturally devoid of such sites or can be designed to eliminate such a site(s). Optionally the non-conserved region in the amplicon comprises at least 10 base pair differences with respect to the sequence amplified with the same primers using *Chlamydia trachomatis* 16S RNA gene (SEQ ID NO: 5) as a template. More preferably the non-conserved region comprises at least 20 base pair differences with respect to the sequence amplified with the same primers using *Chlamydia trachomatis* 16S RNA gene (SEQ ID NO: 5) as a template. The conserved regions to which the primers hybridize comprise at least 18 contiguous base pairs which are at least 80% identical among the at least 10 eubacterial species. More preferably the conserved regions comprises at least 18 contiguous base pairs which are at least 80% identical to PEU7 and PEU 8 (SEQ ID NO: 1 and 2), or PEU 4 and 5 (SEQ ID NO: 3 and 4). Primers which are particularly suitable in the practice of the present invention are PEU 7 and PEU 8 (SEQ ID NO 1 and 2), and PEU 4 and PEU 5 (SEQ ID NO: 3 and 4). These produce amplification products of 416 or 811 basepairs, respectively.

One can amplify without contamination or with much reduced contamination by digesting all of the reagents for amplification with a restriction endonuclease. Alu I is a preferred enzyme although others can also be used. The considerations for selecting an endonuclease are that it should not recognize and cleave within the primer sequences, but it should cleave at least once, twice, or thrice within the amplicon. Any Taq polymerase can be used as is convenient in the particular context. Preferably the polymerase will not be active until heated to about 95 degrees centigrade. Thus nonspecific amplification will not occur, or will not occur to appreciable extent during the restriction digestion phase of the process. The restriction endonuclease can be inactivated using any means known in the art, however, it needs to be a selective means which does not adversely affect the activity of Taq DNA polymerase. Heating the restriction endonuclease for a time and at a temperature sufficient to inactivate it but not the polymerase is preferred. For Alu I, an about 20 minute incubation at about 65 degrees C. may be sufficient. Suitable temperatures range from 55 to 75° C., preferably from 60 to 70° C., more preferably from 62 to 67° C. Suitable times range from 5 to 35 minutes, preferably 10 to 30 minutes, more preferably 15 to 25 minutes. All features need not be used to achieve excellent results. Determination of appropriate inactivation times and conditions for any particular enzyme and reagent mixture is well within the skill of the art.

A test sample is mixed with the reagents for polymerase chain reaction and the mixture is subjected to conditions such that any templates present in the test sample which hybridize to both primers are amplified. Suitable temperatures and times for cycling PCR are known in the art and can be selected by those of skill in the art, depending upon the length and base composition of the template and primers, for example. Amplification product is detected using any techniques known in the art, including electrophoresis, fluorescence of degraded probes (real-time PCR), and detection of incorporated radioactive mononucleotides. A detected amplification product indicates the presence of template which hybridizes to both primers in the test sample.

Suitable test samples include blood, urine, cerebral spinal fluid, stool, tears, saliva, food samples, water samples, samples of ventilation systems, etc. The samples are treated to liberate DNA from any bacteria which may be present. Means for isolating DNA from bacterial samples are well known in the art and any such technique can be used as is desired by the routineer.

If an amplification product is detected, bacteria are indicated as present in the test sample. The identity of the bacteria can be determined by a variety of means. The amplification product can be sequenced and the determined sequence matched with the known sequence of 16S RNA genes from bacteria. Alternatively, a bacterial species can be identified as a source of the templates by restriction endonuclease digestion of the amplification product and determining sizes of products of said digestion. Patterns of digests can be uniquely identified with particular bacterial species. Another alternative technique is to amplify the amplification product or original template in the test sample using primers which are specific, rather than universal, i.e., primers which hybridize to a single eubacterial species' 16S RNA.

Kits for detecting bacteremia in a patient sample can comprise any number of the reagents necessary for carrying out the assay. Some kits contain only primers and a restriction endonuclease. As discussed above, these are selected or designed in tandem so that the primers are not cleaved by the endonuclease but the amplicon is preferably cleaved at least once. Suitable enzymes are those that recognize sites of four, five, or six base pairs. The primers preferably hybridize to and amplify 16S RNA genes from at least 10 eubacterial species. Other reagents which can be included in the kit include deoxyribonucleotides, Taq DNA polymerase, and buffer. Additionally control template can be included, such as from *Chlamydia trichomatis*. The reagents in the kit can be separately packaged or packaged in groups.

EXAMPLES

In these examples we describe a method for removing background bacterial DNA from a PCR assay which employs a highly conserved region of the 16s rRNA (allowing for universal amplification of bacterial species).[1] Results from a prospective clinical study using human whole blood specimens taken from patients with suspected bacteremia in an urban emergency department are reported.

Example 1

Study Design

This was a prospective identity-unlinked investigation. This technique, is a sampling method which allows single point in time patient related data collection with anonymous testing of patient blood samples taken for various blood borne pathogens. In brief, excess serum was retained from patients' 18 years of age and older who presented to The Johns Hopkins Hospital Emergency Department and had blood drawn for blood culture. Enrolled patients were assigned a unique study number, which was used to code the excess sera, as well as the laboratory and descriptive data. Descriptive data included demographics, clinical data, discharge diagnosis, and blood culture findings. After coding, all patient identifiers were stripped. In this way, results of the PCR analysis could not be directly linked to a patient by name or history number. The study was approved by the Johns Hopkins University Institutional Review Board.

Patients and Sample Collection

Practice at our hospital involves collection of at least 2 sets of blood cultures for all patients in whom the treating physician suspects systemic bacterial infection. During a 4-month period 2000 febrile intravenous drug users (all of whom are considered at risk for bacteremia) whom had blood cultures drawn simultaneously had a 3 mL aliquot of whole blood collected for PCR analysis. All patients who had blood drawn for the study had their skin prepped with 2 betadine swabs. Samples were collected in a sterile fashion. Blood obtained for culture was inoculated (5 cc each) into aerobic and anaerobic bottles (BACTEC; Beckton Dickinson, Inc.), and were then sent immediately to the clinical microbiology laboratory for processing.

Samples for PCR analysis were collected by inoculating 3 cc of whole blood into sterile $Na_2$-EDTA tubes. These samples were immediately placed in storage at 4° C. for batch processing at 3-4 weeks intervals. PCR analysis was carried out in the laboratory without knowledge of blood culture results or clinical course of the patient. For purposes of assay refinement and control, 3 ml of blood was also collected from healthy volunteers using standard sterile techniques described above.

DNA Extraction

Bacterial colonies from *Staphylococcus aureus, Streptococcus pneumoniae, Escherichia coli* and *Enterococcus faecalis* were obtained from clinical isolates and resuspended in DEPC $H_2O$ (courtesy of Jim Dick, Director, Clinical Microbiology Laboratory, The Johns Hopkins Hospital). These pathogens were chosen because they are among the more common organisms observed in bacteremic patients who present to the Emergency Department. Each of the 4 bacterial samples were then spiked into whole blood specimens taken from healthy volunteers. These samples were used to optimize the DNA extraction technique and the PCR assay.

DNA was extracted from whole blood samples (taken either from healthy volunteers spiked with bacterial isolates, or from patient specimens) using a phenol-chloroform-isoamyl alcohol extraction procedure. An aliquot of 200 µl of whole blood was diluted in 450 µl DEPC water. The solution was incubated at room temperature for 10 min with occasional mixing. 40 µl proteinase K and 15 µl 5.0 mM NaCl was added to the solution and incubated at 55° C. for 30 min. Subsequently, one ml phenol-chloroform-isoamyl alcohol (25:20:1) was added and gently mixed, followed by centrifugation at 13000 rpm for 15 min. Approximately 300 ul of the aqueous layer was aliquoted into 1 ml of 100 proof ethanol. Samples were centrifuged at 13,000 rpm for 15 min, washed with 1 mL 70% ethanol, and air-dried. The DNA pellet was then re-suspended in 100 µl DEPC water.

Primer Selection

Figure 1A:
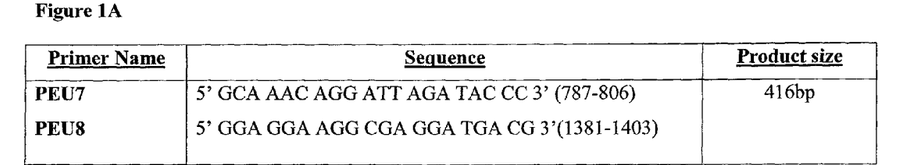

PCR primers were designed from conserved regions of the 16S rRNA gene. Oligonucleotides were synthesized and purified on a DNA synthesizer 380 (Applied BioSystems, CT) at The Johns Hopkins University Genetic Core Laboratory. FIG. 1a shows the primer pairs, sequences, and size of the amplified product after PCR.

Restriction Endonuclease Digestion

Prior to amplification of the desired target DNA, all PCR reagents (HotStarTaq DNA polymerase, primers, dNTPs, $MgCl_2$, and PCR buffer) were treated with the restriction endonuclease, AluI. The targeted product contains four sites for AluI, which is extremely specific for the nucleotide sequence $AG_\uparrow CT$, cleaving the sequence in the center as indicated by an arrow. No sites for AluI exist in the PCR primers themselves. Predigestion of PCR reagents thus digests all potential contaminant or background DNA in the PCR master mixture while leaving the primer set intact.

The 100 ul PCR reaction cocktail contained 2.5 units of HotStarTaq DNA polymerase (QIAGEN, Inc.) 25 pmol of each primer, 200 µM of each nucleotide, 4 mM $MgCl_2$, and 1×PCR buffer (QIAGEN, Inc.). Restriction digestion with AluI was carried out by adding 10.0 units of enzyme to each 100 µl PCR reaction and incubating at 37° C. for 1.5 hours, to allow for complete digestion of endogenous background DNA. Inactivation of restriction enzyme was achieved by heating to at 65° C. for 30 min. prior to the addition of target DNA for PCR amplification.

PCR Amplification and Detection of Products

PCR with broad-range 16S rRNA gene primers was performed using 10 µl target DNA in each 100 µl PCR reaction. The reaction consisted of a heat-mediated enzyme activation step at 95° C. for 10 min, and 35 cycles of amplification in a Perkin-Elmer Gene-Amp 2400 Thermal Cycler with the following conditions for each cycle: denaturation at 95° C. for 30 sec, annealing at 58° C. for 45 sec, and extension at 72° C. for 90 sec. Finally, the elongation step was performed at 72° C. for 7 min and the final amplified product stored at 4° C. until further processing. Amplified products were detected by gel electrophoresis on a 3% agarose gel stained with ethidium bromide. The gel was visualized under UV-light for the presence of an 416-bp band and photographed for documentation.

Sequencing

Amplified products were sequenced using the automated fluorescent DNA Sequencer (Perkin Elmer, Inc.) to confirm the identity of the spiked pathogens.

Blood Culture Results and Clinical Data

Blood culture findings, final clinical data, duration of antibiotic therapy, and final discharge diagnosis were retrieved from the electronic patient record (EPR) system at The Johns Hopkins Hospital. Patients with single isolates of coagulase negative Staphylococci were excluded from analysis, as this is a common contaminant in blood culture bottles, and it was impossible to determine whether the source of the single positive blood culture was identical to the blood sample used for PCR analysis.

Statistical Analysis

Sensitivity, specificity, positive predictive value (PPV) and negative predictive value (NPV) were calculated by the method developed by Ransoff and Feinstein. The false-positive rate, false-negative rate, and accuracy were also calculated. Each calculated value was expressed as a percentage.

Example 2

This example demonstrates the contamination present in PCR reagents and the efficacy of the subject method for destroying the contaminants.

Figure 1B:
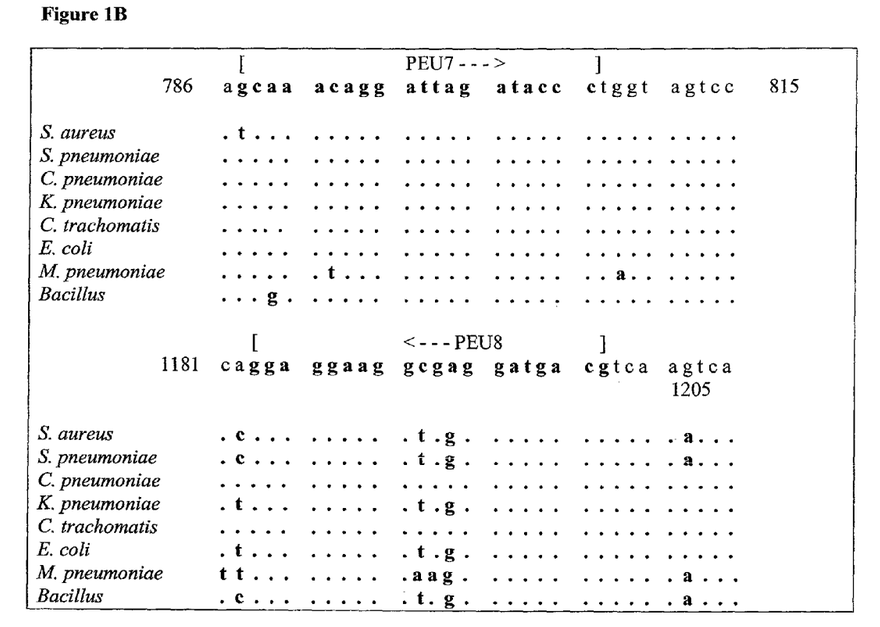
FIG. 1B. Alignment of target sequences (SEQ ID NO: 6 and SEQ ID NO: 7) of primer set PEU7 and ≠PEU8, respectively, designed from the 16rRNA gene of *S. aureus* with the 16S rRNA genes of other pathogens. A dot indicates the same base, and a letter indicates a base different from that in the primer set.
Figure 2:
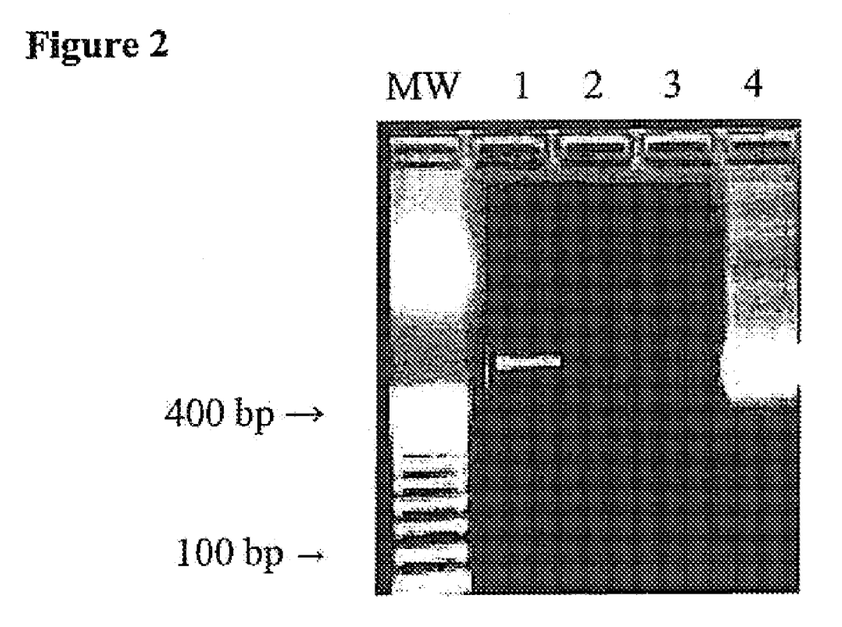
FIG. 2 shows the effect of restriction enzyme digestion on contamination in the PCR system. PCR amplification using 16S rRNA primers. Molecular weight marker is indicated MW. Lane 1 is a PCR amplification using the PEU 7/8 primer pair, with no added bacteria. Lane 2 is the identical amplification with Alu I predigestion of the PCR cocktail. Lane 3 is a PCR amplification using DNA purified from whole blood taken from a healthy human donor, again with an Alu I predigestion step. Lane 4 is the same as Lane 3 with purified *E. coli* bacteria spiked into human blood.

The PCR amplification assay was first tested in a mock sample containing water, with no added bacteria to determine whether the reagents themselves contained contaminating sources of bacterial DNA that might lead to false-positive results. FIG. 2 shows results of a PCR amplification using the 16S rRNA primers described in FIG. 1. Lane 1 shows a product of the expected size, indicating that contaminant bacterial DNA is being amplified in our system. The effect of a predigestion step, in which AluI at is added to all components of the PCR cocktail is shown in Lane 2. (Titration of AluI from 1-20 U/reaction identified 10 U/reaction to be the optimal enzyme concentration.) Lane 3 shows results of a PCR amplification carried out using whole blood taken from a healthy control, with no bacteria added, again showing the absence of a signal. Lane 4 is a positive control, with spiked bacterial pathogen from *E. coli*.

Example 3

This example demonstrates the successful practice of the method using known bacteria spiked into test samples.

Figure 3:
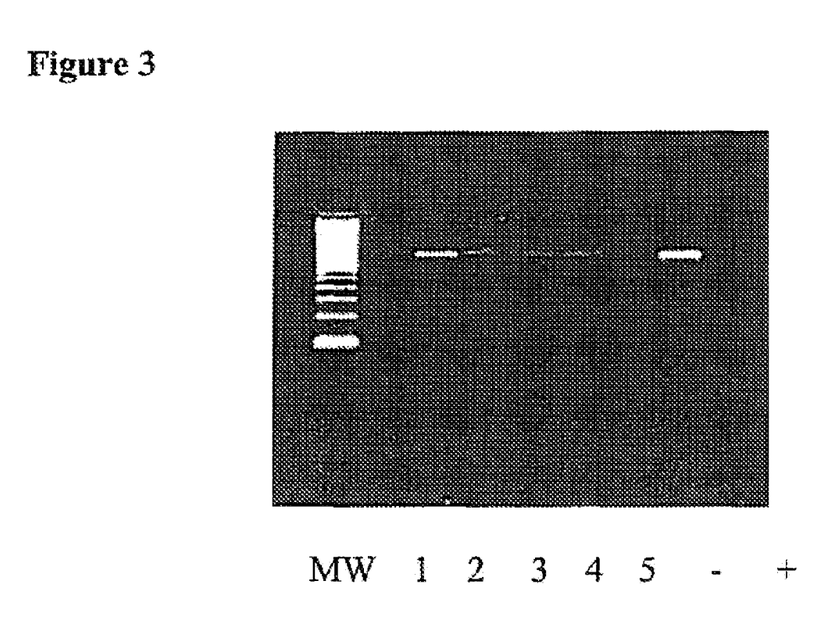
FIG. 3 shows PCR amplification of common bacterial isolates. Healthy donor blood spiked with known bacterial isolates: DNA was extracted and PCR amplification was carried out using conserved 16SrRNA primers. Molecular weight marker is indicated by MW. Lane 1 is whole blood with no bacteria added; Lane 2-5 contain whole blood spiked with *E. coli, E. faecalis, S. aureus* and *S. pneumonia* respectively. Lane 6 is whole blood with no bacteria added; Lane 7 is a positive control in which bacterial DNA was purified from *E. Coli* colonies and subjected to PCR amplification. All PCR reactions were pretreated with AluI prior to amplification.

Healthy human whole blood was next spiked with 1 of 4 bacterial isolates and DNA was then extracted. A series of PCR amplifications reactions were subsequently carried out with the decontamination step, described above included, i.e., all PCR reagents were pretreated with the restriction enzyme, Alu I at 10 U/reaction prior to amplification. FIG. 3 shows the PCR amplified products from the whole blood specimens, as well as the negative control samples, in which no bacteria was added prior to PCR amplification. The amplified product of 411 base pairs was detected for each of the spiked reactions. DNA sequencing correctly confirmed the identity of each spiked pathogen.

Example 4

This example demonstrates the limit of detection of bacteria in the disclosed assay system.

A titration profile was carried out to determine the limits of detection of the PCR assay.

Figure 4:
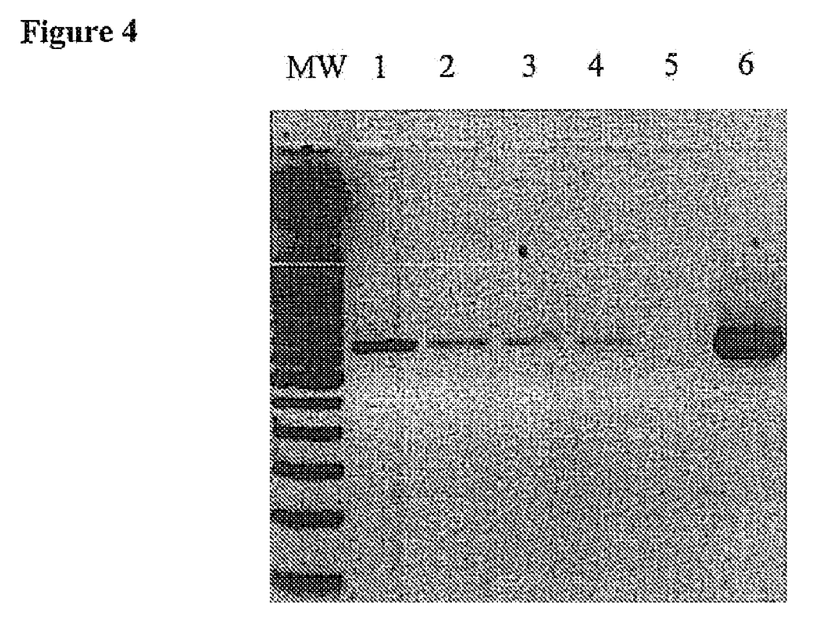
FIG. 4 shows detection limits of PCR system. *E. coli* bacteria were diluted in dd $H_2O$; OD was measured. Serial dilutions were then performed, followed by DNA isolation and PCR amplification using PEU 7/8 primer pair. All PCR reactions were pretreated with AluI prior to amplification. Concentrations are 500, 50, 10 and 5 colonies/PCR, for lanes 1-4. Molecular weight marker is indicated as MW. Lane 5 is a negative control. Lane 6 is a positive control.

Healthy human blood was spiked with *E. coli* at concentrations ranging from 500 to 5 bacteria/sample. FIG. 4 demonstrates the limit of detection for this assay at 5 bacteria/PCR reaction.

Example 5

This example demonstrates the successful practice of the assay method on actual clinical samples.

Figure 5:
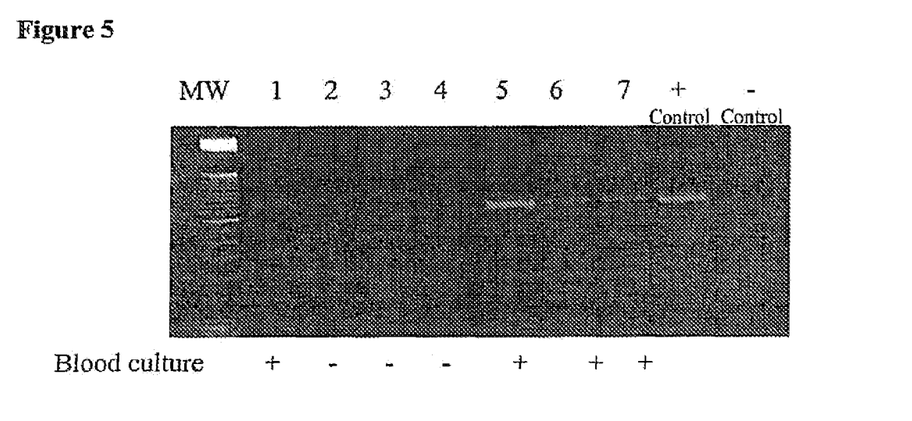
FIG. 5 shows a representative gel taken from clinical trial. Whole blood was taken from febrile patients with suspected bacteremia. DNA was isolated and PCR amplification carried out using PEU 7/8 primer pair. All PCR reactions were pretreated with AluI prior to amplification. Lanes 1-7 were taken from patient samples; '+' refers to positive control, which is a PCR amplification of DNA isolated from purified *E. coli* bacteria; '−' refers to negative control, which is a PCR amplification of a mock DNA isolate. Blood culture findings for the seven clinical samples are indicated as + (positive) or − (negative), below the figure.

DNA was next isolated from whole blood specimens from 60 patients with suspected bacteremia. Valid data for complete analysis was available for 51 patients; 7 were excluded due to a single positive coagulase negative Staphylococci; 1 was excluded due to a missing blood culture report and 1 was excluded due to missing clinical data. The products of PCR amplification were separated on an agarose gel for these 51 patients, and compared with blood culture results. A representative gel with 7 patient samples is shown in FIG. 6. Table 1 summarizes patient data and includes PCR results, blood culture findings and clinical data. Discrepancies between blood culture findings and PCR results occurred in 7 cases. Table 2 shows correlation of PCR and blood culture results in terms of sensitivity (86.7%), specificity (86.9%), PPV (76.4%) and NPV (94.1%).

TABLE 1

51 patients with blood culture, PCR and blood culture results, duration of antibiotic treatment and discharge diagnosis.

| Pt # | PCR | BloodCx | #times+ | Organism | No. days IV Ab | No. days po Ab | Discharge Diagnosis |
|---|---|---|---|---|---|---|---|
| 1 | N | N | — | — | 3 | 14 | Cellulitis/Abscess |
| 2 | P | P | 4 | *S. Aureus* | 28 | — | Infective Endocarditis |
| 3 | P | P | 2/1 | *S. Viridians/ S. Aureus* | 28 | — | Infective Endocarditis |
| 4 | N | P | 1/1 | Strep G/ *Propionobacterium* | 42 | — | Septic Arthritis/ Pneumonia |
| 5 | N | N | — | | 2 | 7 | Leg ulcer |
| 6 | N | N | — | | 2 | 12 | Pelvic inflammatory disease |
| 7 | N | N | — | | 4 | 14 | Neck abscess |
| 8 | N | N | — | | 1 | — | Bronchitis |
| 9 | P | P | 2 | Strep GA | 42 | — | Infective Endocarditis |
| 10 | P | N | — | | 3 | 7 | Urinary tract infection/?Pyelonephritis |
| 11 | P | N | — | | 2 | 14 | Cellulitis/Abscess |
| 12 | N | N | — | | 4 | 10 | Cellulitis/Abscess |
| 13 | P | P | 2 | *S. Viridians* | 55 | — | Infective Endocarditis |
| 14 | N | N | — | | 7 | 7 | Cellulitis/Abscess |
| 15 | P | P | 3 | Strep GA | 14 | — | Bacteremia/Cellulitis |
| 16 | N | N | — | | 2 | 12 | Pneumonia |
| 17 | P | P | 2 | *S. Aureus* | 28 | — | Infective Endocarditis |
| 18 | N | N | — | | 1 | 13 | Abscess |
| 19 | P | P | 3 | *S. Aureus* | 42 | — | Infective Endocarditis |
| 20 | P | P | 3 | *S. Aureus* | 42 | — | Infective Endocarditis |
| 21 | P | P | 2 | *E. coli/ Corynebacterium* | 5 | 9 | Bacteremia/Pyelonephritis |
| 22 | P | N | — | | 2 | 12 | Cellulitis/Abscess |
| 23 | P | N | — | | 53 | 18 | Abscess (+end stage renal disease) |
| 24 | N | N | — | | 4 | 10 | Pneumonia |
| 25 | N | N | — | | 2 | 12 | Urinary tract infection |
| 26 | P | P | 1 | *S. Viridians* | 1 | — | Fever unknown origin; left against medical advise |
| 27 | N | N | — | | 2 | 8 | Pneumonia |
| 28 | N | N | — | | 1 | — | Drug fever |
| 29 | N | N | — | | 2 | 8 | Ulcer |
| 30 | N | N | — | | 0 | 0 | Drug fever |
| 31 | N | N | — | | 2 | 8 | Sinusitis |
| 32 | N | N | — | | 3 | 7 | Pneumonia |
| 33 | N | N | — | | 1 | — | Drug fever |
| 34 | N | N | — | | 3 | 11 | Cellulitis/Abscess |
| 35 | N | N | — | | 0 | 0 | Drug fever |
| 36 | N | N | — | | 1 | 13 | Cellulitis |
| 37 | N | N | — | | 1 | 7 | Bronchitis |
| 38 | N | N | — | | 5 | 6 | Pneumonia |
| 39 | N | N | — | | 2 | 10 | Cellulitis/abscess |
| 40 | N | N | — | | 2 | 2 | Urinary tract infection |
| 41 | P | P | 1 | *Propionobacterium* | 2 | — | Drug fever |
| 42 | N | P | 1 | *Coryneybacterium* | 1 | 9 | Cellulitis |
| 43 | N | N | 2 | | 9 | — | Abscess/Catheter infection |
| 44 | P | P | 2 | *Enterobacterium Actinobacterium* | Check | — | Urosepsis |
| 45 | N | N | — | | 2 | — | Drug fever |
| 46 | P | P | 3 | Strep Group A | 28 | — | Infective endocarditis |
| 47 | N | N | — | | 1 | — | Bronchitis |

TABLE 1-continued 51 patients with blood culture, PCR and blood culture results, duration of antibiotic treatment and discharge diagnosis.

| Pt # | PCR | BloodCx | #times+ | Organism | No. days IV Ab | No. days po Ab | Discharge Diagnosis |
|---|---|---|---|---|---|---|---|
| 48 | N | N | — |  | 1 | — | Drug fever |
| 49 | N | N | — |  | 1 | — | Splenic laceration |
| 50 | N | N | — |  | 7 | 3 | Pneumonia |
| 51 | N | N | — |  | 5 | 5 | Pneumonia |

TABLE 2

Correlation between PCR findings and standard blood culture results. Number of blood samples with the following results obtained:

| | by Blood Culture | | |
|---|---|---|---|
| by PCR | Positive | Negative | Total |
| Positive | 13 (a) | 4 (b) | 17 |
| Negative | 2 (c) | 32 (d) | 34 |
| Total | 15 | 36 | 51 |

Sensitivity was calculated as $[a/(a+c)] = 13/15 = 86.7\%$; Specificity was calculated as $[d/(b+d)] = 32/36 = 88.9\%$; Positive predictive value (PPV) was calculated as $[a/(a+b)] = 13/17 = 76.4\%$; Negative predictive value (NPV) was calculated as $[d/(c+d)] = 32/34 = 94.1\%$; False-positive rate was calculated as $[b/(a+b+c+d)] = 5/51 = 9.8\%$; False-negative rate was calculated as $[c/(a+b+c+d)] = 2/51 = 3.9\%$, and accuracy was calculated as $[(a+d)/(a+b+c+d)] = 45/51 = 88.2\%$.

Microbial contamination can be derived from multiple sources, including laboratory equipment, tubes, Taq DNA polymerase, or any other component of the PCR cocktail. Restriction endonuclease digestion has previously been described as a method for elimination of false-positives. The earliest reported use of this technique was to eliminate nonspecific amplification, or spurious binding of primers to nearly homologous target sites in genomic DNA, with a PCR assay for human papilloma virus detection in cervical specimens. Importantly, the amplification target was not the 16S rRNA gene, where contamination is particularly problematic due to multiple copies, and the highly conserved character of this gene. More recently decontamination studies have focused on the recognized presence of bacterial DNA in Taq DNA polymerase, with Carroll et al reporting effective elimination of false-positives, by pretreatment of the Taq DNA polymerase with a restriction enzyme that could later be heat inactivated. While promising, the methodology described did not permit decontamination of all components of the PCR cocktail and, as of yet, has not been tested in a clinical trial. Of interest a recent report from Corless et al describing restriction endonuclease digestion for elimination of false positives in a real-time universal 16S rRNA PCR reaction, failed to show consistent decontamination. Possible explanations for this finding include presence of background contaminating DNA that were not digested by the particular restriction enzyme chosen and relative inhibition of Taq DNA polymerase which may have been caused during inactivation of the restriction enzyme. Other decontamination methodologies which were described and remain under investigation included UV irradiation and DNase digestion, either alone or in combination with restriction endonuclease digestion.

The restriction enzyme we chose, Alu I, was selected because it is not encoded for in the 16S rRNA primer pair, but has several, four, sites within the amplicon. The presence of multiple sites in the amplicon targeted by our primer pair increases the likelihood of complete digestion of contaminating sources of bacterial DNA. Furthermore, selection of an enzyme which has no sites in the primer pair itself, permits decontamination of the entire PCR cocktail, including the primer set itself, prior to the amplification. These 2 features may in part account for the efficacy of the predigestion step demonstrated in FIG. 2, and the relatively high sensitivity of our assay with detection of as little as 5 bacteria/PCR reaction.

Previous investigators have recognized the potential impact of PCR technology for clinical practice. A variety of assays for species-specific infectious agents have been developed with several reaching commercial availability, including those for *Mycobacterium tuberculosis*, *Chlamydia trachomatis*, *Mycoplasma pneumonia*, *Neisseria gonorrhea*, herpes simplex virus and cytomegalovirus. In clinical practice PCR is considered the method of choice for only a very few specific clinical circumstances (e.g. detection of herpes simplex virus or enteroviruses in cerebrospinal fluid). More frequent applications of PCR assays are as an adjunct to standard culture, for example in patients with suspected tuberculosis, allowing faster time to diagnosis and treatment. Widespread utilization of PCR techniques in routine practice however, awaits further improvement in assay performance and validation of sensitivity and specificity in clinical trials.

One clinical situation where PCR could be used is for rapid detection of bacteremia, which would be invaluable in disposition and therapeutic decision-making. Exploiting the existence of highly conserved regions of DNA common to all bacterial species allows one to design primers for a PCR assay that could serve as a screening tool for systemic bacterial infection. Published clinical trials with such universal PCR assays, have included early detection of bacteremia in febrile neonates and neutropenic cancer patients, as well as critically ill patients in the intensive care unit, all considered at high risk for systemic infection. While several of these studies offer promising results, technical concerns have prevented general acceptance of these assays for routine use. One of the most frequently cited factors which have slowed the development of universal PCR amplification assays is the problem of ubiquitous nonspecific bacterial contamination present in the environment or the PCR reagents resulting in significant number of false-positive results. This nonspecific amplification of background DNA is particularly problematic for a broad spectrum primer, such as the 16S rRNA, due its high conservation as well and its presence in multiple copies.

In addition to testing the enzymatic decontamination step in human blood samples spiked with bacterial isolates, we also pilot tested the PCR assay in a clinical trial. We found that 13 of 15 culture positive blood specimens were PCR positive, with the universal primers we used, giving a sensitivity of 86.6%. The 2 cases which were positive by blood culture, but negative by PCR were from gram-positive organisms (one was *Corynebacterium* and the other contained mixed organisms including Streptococci Group G, *Propionobacterium* and coagulase negative Staphylococci. Clinically, the patient who grew out *Corynebacterium* was treated for a localized cellulitis. Organisms grew from the aerobic bottle of only 1/3 sets of cultures sent, and was believed to be a contaminant by the treating physicians. Thus it is likely that this patient may not have been bacteremic. The other blood culture positive, PCR negative patient had septic arthritis of the knee and developed pneumonia later during the hospitalization. Streptococci Group G organisms grew from the anaerobic bottle of one blood culture at 2 days, and *Propionobacterium* grew from one anaerobic bottle after 7 days. This was likely a case of early bacteremia which was missed by PCR. A possible explanations for the missed cases include inadequate lysis of the bacterial cell wall which has been previously described. Alternative explanations which might have led to this false-negative findings relate to specimen handling and processing, such as loss of DNA during the DNA extraction procedure, or DNA degradation during storage of blood. Collection of several blood samples which could be used for both culture and PCR testing may help to resolve such discrepancies in future studies; additionally specimen handling errors could be limited by restricting storage time of specimens and DNA quantification after extraction, prior to running the PCR assay.

For the four cases that were PCR positive, but culture negative all had clinically identifiable infections, three with cellulitis and/or abscess and one with urinary tract infection and possible pyelonephritis (see Table 1). All of them received antimicrobial therapy for at least seven days based on clinical appearance. Possible explanations for the discordant findings in these cases include improved sensitivity of the PCR assay over standard blood culture, for detection of early bacteremia, or false-positive PCR results. Since there is no true 'gold-standard' test, the approach of interpreting the clinical picture and likelihood of systemic infection has been used as a proxy. However, this method is inherently subjective. Alternative approaches include sequencing the PCR product and correlating findings with the likely pathogen, based on site of infection, or other specimen examination such as sputum, swab or gram stain.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

REFERENCES

1. Centers for Disease Control and Prevention. Increase in national hospital discharge survey rates for septicemia—United States. *MMWR, Morb Mort Wkly* Rep. 1990; 39: 31-34.
2. Price P. Evaluation of clinical practice guidelines on outcome of infection in patients in the surgical intensive care units. *Crit. Care Med* 1999; 27(10) 2118. RR Find others
3. Sands K E, Bates D W, Lanken P N, et al. Epidemiology of sepsis syndrome in 8 academic medical Centers. *JAMA* 1997; 278; 234-240.
4. Kuppermann, N. Occult bacteremia in young febrile children. *Pediatr Clin North Am* 1999 46(6): 1073-1079.
5. Samet J H, Shevitz A, Fowle J, Singer D E. Hospitalization decision in febrile intravenous drug users. *American Journal of Medicine* 1990; 89: 53-56.
6. Bennedsen J, Thomsen V O, Pfyffer G E, et al. Utility of PCR in diagnosing pulmonary tuberculosis. *J Clin Micro* 1996; 34: 1407-1411.
7. Zhang Y, Isaacman D J, Wadowsky R M, et al. Detection of *Streptococcus pneumoniae* in whole blood by PCR. *J Clin Micro* 1995; 33: 596-601.
8. Wilson K H, Blitchington R B, Greene R C. Amplification of bacterial 16S ribosomal DNA with polymerase chain reaction. *J Clin Micro* 1990; 323: 1573-1580.
9. McCabe K M, Khan G, Zhang Y-H, et al. Amplification of bacterial DNA using highly conserved sequences: automated analysis and potential molecular triage of sepsis. *Pediatrics* 1995; 95(2): 165-169.
10. Ley B E. Detection of bacteremia in patients with fever and neutropenia using 16S rRNA gene amplification by PCR. *Eur J Clin Microbiol Infect Dis* 1998; 17(4): 247-253.
11. Kane T D, Alexander J W, Johannigman A. The detection of microbial DNA in the blood: A sensitive method for the detection of bacteremia and/or bacterial translocation in surgical patients. *Ann Surg* 1997; 227: 1-9.
12. Goldenberger D, Kunzli A, Vogt P, et al. Molecular diagnosis of bacterial endocarditis by broad-range PCR amplification and direct sequencing. *J Clin Micro* 1997; 35(11): 2733-2739.
13. Rantakokko-Jalava K, Nikkari S, Jalava J, et al. Direct amplification of rRNA gene in diagnosis of bacterial infections. *J Clin Micro* 2000; 38; 32-39.
14. Sharma J K, Gopalkrishna V and Das B C. A simple method for elimination of unspecific amplifications in polymerase chain reaction. *Nucl Acids Res* 1992; 20: 6117-6118.
15. Carroll N M, Adamson P and Okhravi N. Elimination of bacterial DNA from Taq DNA polymerases by restriction endonuclease digestion. *J Clin Micro* 1999; 37: 3402-3404.
16. Corless C E, Guiver M, Borrow R. Contamination and sensitivity issues with a real-time universal 16S rRNA PCR. *J Clin Micro* 200; 38: 1747-1752.
17. Ou C Y. Use of UV irradiation to reduce false positivity in polymerase chain reaction. 1991; *Bio Techniques* 10: 442-444.
18. Hilali F, Saulnier E. Chachaty E et al. Decontamination of polymerase chain reaction reagents for detection of low concentrations of 16S rRNA genes. *Mol Biotechnol* 7: 207-216.
19. Post J C, Ehrlich G. The impact of the polymerase chain reaction in clinical medicine. *JAMA* 2000; 283(12): 1544-1546.
20. Louie M, Louie L, Simor A. The role of DNA amplification technology in the diagnosis of infectious disease. *CMAJ* 2000; 163(3): 301-309.
21 Altwegg M, Kayser F H. Will cultures survive? The role of molecular tests in diagnostic bacteriology. *Infection* 1997; 25(5): 265-268.
21. Schluger N W. The polymerase chain reaction in the diagnosis and evaluation of pulmonary infections. *Am J Respir Crit. Care Med* 1995; 152(1): 11-16.
22. Fredricks D N and Relman D A. Application of polymerase chain reaction to the diagnosis of infectious diseases. *Clin Infect Dis* 2000; 29: 475-486.
23. Fredricks D N and Reiman D A. Improved amplification of microbial DNA from blood cultures by removal of the PCR inhibitor sodium polyanetholesulfonamate. 1998 *J Clin Micro;* 26: 2810-2816.
24. Cursons R T M. Jeyerajah E and Sleigh J W. The use of polymerase chain reaction to detect septicemia in critically ill patients. *Crit. Care Med* 1999; 27: 937-943. RR find other as well.

We claim:

1. A pair of polymerase chain reaction primers for amplifying a 16S rRNA gene of eubacteria selected from the group consisting of: PEU 7 and PEU 8 (SEQ ID NO: 1 and 2); and PEU 4 and PEU 5 (SEQ ID NO: 3 and 4).

* * * * *

UNITED STATES PATENT AND TRADEMARK OFFICE
CERTIFICATE OF CORRECTION

PATENT NO. : 8,288,524 B2
APPLICATION NO. : 12/849474
DATED : October 16, 2012
INVENTOR(S) : Richard E. Rothman et al.

It is certified that error appears in the above-identified patent and that said Letters Patent is hereby corrected as shown below:

On the Title Page, Item (75):
Please change the residency information for Richard E. Rothman from "Cockekysville, MD" to --Cockeysville, MD--

Signed and Sealed this
Thirteenth Day of August, 2013

Teresa Stanek Rea
*Acting Director of the United States Patent and Trademark Office*

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: synthetic amplification primer

<400> SEQUENCE: 1
gcaaacagga ttagataccc                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic amplification primer

<400> SEQUENCE: 2
ggaggaaggc gaggatgacg                                               20

<210> SEQ ID NO 3
<211> LENGTH: 22
<212> TYPE: DNA
<213> ORGANISM: Artificial Sequence
<220> FEATURE:
<223> OTHER INFORMATION: synthetic amplification primer

<400> SEQUENCE: 3
acaaggcccg agaacgtatt ca                                            22

<210> SEQ ID NO 4
<211> LENGTH: 21
<212> TYPE: DNA
<213> ORGANISM: Artificial Sequence
<220> FEATURE:
<223> OTHER INFORMATION: synthetic amplification primer

<400> SEQUENCE: 4
gtgccagcag cagcggtaat a                                             21

<210> SEQ ID NO 5
<211> LENGTH: 1550
<212> TYPE: DNA
<213> ORGANISM: Chlamydia trichomatis

<400> SEQUENCE: 5
ctgagaattt gatcttggtt cagattgaac gctggcggcg tggatgaggc atgcaagtcg    60
aacggagcaa ttgtttcgac gattgtttag tggcggaagg gttagtaatg catagataat   120
ttgtccttaa cttgggaata acggttggaa acgccgcta ataccgaatg tggcgatatt    180
tgggcatccg agtaacgtta aagaagggga tcttaggacc tttcggttaa gggagagtct   240
atgtgatatc agctagttgg tggggtaaag gcctaccaag gctatgacgt ctaggcggat   300
tgagagattg gccgccaaca ctgggactga gacactgccc agactcctac gggaggctgc   360
agtcgagaat ctttcgcaat ggacggaagt ctgacgaagc gacgccgcgt gtgtgatgaa   420
ggctctaggg ttgtaaagca ctttcgcttg gaataagag aagacggtta ataccgctg    480 gatttgagcg taccaggtaa agaagcaccg gctaactccg tgccagcagc tgcggtaata   540
cggagggtgc tagcgttaat cggatttatt gggcgtaaag gcgtgtagg cggaaaggta   600

-continued

```
agttagttgt caaagatcgg ggctcaaccc cgagtcggca tctaatacta tttttctaga    660
ggatagatgg agaaagggga atttcacgtg tagcggtgaa atgcgtagat atgtggaaga    720
acaccagtgg cgaaggcgct tttctaattt atacctgacg ctaaggcgcg aaagcaaggg    780
gagcaaacag gattagatac cctggtagtc cttgccgtaa acgatgcata cttgatgtgg    840
atggtctcaa ccccatccgt gtcggagcta acgcgttaag tatgccgcct gaggagtaca    900
ctcgcaaggg tgaaactcaa aagaattgac ggggccccgc acaagcagtg gagcatgtgg    960
tttaattcga tgcaacgcga aggaccttac ctgggtttga catgtatatg accgcggcag   1020
aaatgtcgtt ttccgcaagg acatatacac aggtgctgca tggctgtcgt cagctcgtgc   1080
cgtgaggtgt tgggttaagt cccgcaacga gcgcaaccct tatcgttagt tgccagcact   1140
tagggtggga actctaacga gactgcctgg gttaaccagg aggaaggcga ggatgacgtc   1200
aagtcagcat ggcccttatg cccagggcga cacacgtgct acaatggcca gtacagaagg   1260
tggcaagatc gcgagatgga gcaaatcctc aaagctggcc ccagttcgga ttgtagtctg   1320
caactcgact acatgaagtc ggaattgcta gtaatggcgt gtcagccata acgccgtgaa   1380
tacgttcccg ggccttgtac acaccgcccg tcacatcatg ggagttggtt ttaccttaag   1440
tcgttgactc aacccgcaag ggagagaggc gcccaaggtg aggctgatga ctaggatgaa   1500
gtcgtaacaa ggtagcccta ccggaaggtg gggctggatc acctccttt              1550
```

```
<210> SEQ ID NO 6
<211> LENGTH: 30
<212> TYPE: DNA
<213> ORGANISM: Artificial Sequence
<220> FEATURE:
<223> OTHER INFORMATION: synthetic amplification primer

<400> SEQUENCE: 6
agcaaacagg attagatacc ctggtagtcc                                      30

<210> SEQ ID NO 7
<211> LENGTH: 30
<212> TYPE: DNA
<213> ORGANISM: Artificial Sequence
<220> FEATURE:
<223> OTHER INFORMATION: synthetic amplification primer

<400> SEQUENCE: 7
caggaggaag gcgaggatga cgtcaagtca                                      30
```